United States Patent
Kotanko et al.

(10) Patent No.: US 11,565,028 B2
(45) Date of Patent: Jan. 31, 2023

(54) TECHNIQUES FOR NON-INVASIVE DETERMINATION OF ESTIMATED CARDIAC OUTPUT DURING DIALYSIS TREATMENT

(71) Applicant: Fresenius Medical Care Holdings, Inc., Waltham, MA (US)

(72) Inventors: Peter Kotanko, New York, NY (US); Stephan Thijssen, New York, NY (US); Israel Campos, Morelia (MX); Hanje Zhang, Rutherford, NJ (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 400 days.

(21) Appl. No.: 16/939,312

(22) Filed: Jul. 27, 2020

(65) Prior Publication Data

US 2022/0023516 A1 Jan. 27, 2022

(51) Int. Cl.
*A61M 1/16* (2006.01)
*A61M 1/14* (2006.01)
(Continued)

(52) U.S. Cl.
CPC ............. *A61M 1/1601* (2014.02); *A61B 5/02* (2013.01); *A61B 5/029* (2013.01);
(Continued)

(58) Field of Classification Search
CPC .... A61M 1/14; A61M 1/1601; A61M 1/1613; A61M 1/34; A61M 1/3624;
(Continued)

(56) References Cited

U.S. PATENT DOCUMENTS

| | | |
|---|---|---|
| 6,746,415 B1 | 6/2004 | Steuer et al. |
| 7,175,809 B2 | 2/2007 | Gelfand et al. |
| 2009/0043171 A1 | 2/2009 | Rule |

OTHER PUBLICATIONS

International Search Report and Written Opinion for the International Patent Application No. PCT/US2021/042463, dated Oct. 19, 2021, 21 pages.

(Continued)

*Primary Examiner* — John Kim
(74) *Attorney, Agent, or Firm* — KDB Firm PLLC (57) ABSTRACT

Techniques and apparatuses for determining an estimated cardiac output for a patient during dialysis treatment are described. In one embodiment, for example, an apparatus may include a memory and logic coupled to the memory. The logic may be configured to determine an upper body oxygen consumption for a patient, determine, during a dialysis process: a hemoglobin concentration and a venous oxygen saturation measured via an optical blood monitor operably coupled to an extracorporeal circuit of a dialysis system performing the dialysis process; an arterial oxygen saturation measured via a pulse oximeter operably coupled to the extracorporeal circuit; an arterial-venous oxygen content difference based on the arterial oxygen saturation and the venous oxygen saturation; and an upper body blood flow (UBBF) as (upper body oxygen consumption)/(arterial-venous oxygen content difference), and determine a treatment recommendation based on the upper body blood flow. Other embodiments are described.

20 Claims, 6 Drawing Sheets

(51) Int. Cl.
  *A61M 1/34*   (2006.01)
  *A61M 1/36*   (2006.01)
  *A61B 5/02*   (2006.01)
  *A61B 5/029*  (2006.01)
  *A61B 5/08*   (2006.01)
  *A61B 5/145*  (2006.01)
  *A61B 5/1455* (2006.01)
  *A61B 5/00*   (2006.01)

(52) U.S. Cl.
  CPC ........ *A61B 5/02028* (2013.01); *A61B 5/0816* (2013.01); *A61B 5/14535* (2013.01); *A61B 5/14542* (2013.01); *A61B 5/14551* (2013.01); *A61B 5/14557* (2013.01); *A61B 5/4836* (2013.01); *A61B 5/7275* (2013.01); *A61M 1/14* (2013.01); *A61M 1/1613* (2014.02); *A61M 1/34* (2013.01); *A61M 1/3624* (2013.01); *A61M 2205/52* (2013.01); *A61M 2230/205* (2013.01)

(58) Field of Classification Search
  CPC ...... A61M 2205/33; A61M 2205/3303; A61M 2205/3306; A61M 2205/331; A61M 2205/3313; A61M 2205/3375; A61M 2205/52; A61M 2230/005; A61M 2230/205; A61M 2230/207; A61B 5/0075; A61B 5/02; A61B 5/0816; A61B 5/14551; A61B 5/4836; A61B 5/02028; A61B 5/029; A61B 5/14535; A61B 5/14542; A61B 5/14557; A61B 5/7275
  See application file for complete search history.

(56) References Cited

OTHER PUBLICATIONS

Ruan, Z.S., et al., "Monitoring Tissue Blood Oxygen Saturation in the Internal Jugular Venous Area Using Near Infrared Spectroscopy," Genet Mol Res 14(1):2920-2928 (Mar. 2015).

FIG. 1

| | Mass | Blood Flow | | Max Blood Flow | O₂ Consumption | | A-V Difference | Resistance |
|---|---|---|---|---|---|---|---|---|
| | kg | ml/min | ml/min/100 g | ml/min | ml/min | ml/min/100g | ml O₂/100ml | kPa/L·min/kg |
| Brain | 1.4 | 750 | (54) | 1500 | 46 | (3.3) | 6.2 | 24.4 |
| Heart | 0.3 | 250 | (83) | 1200 | 29 | (9.7) | 11.4 | 15.7 |
| Skeletal Muscle | 31 | 840 | (2.7) | 20000 | 50 | (0.2) | 6 | 482 |
| Kidney | 0.3 | 1260 | (420) | 1500 | 18 | (6.0) | 1.4 | 3.1 |
| Skin | 3.6 | 460 | (13) | 4000 | 12 | (0.3) | 2.5 | 101 |
| Liver | 2.6 | 1500 | (58) | 4000 | 51 | (2.0) | 3.4 | 22.7 |
| Other | 23.8 | 340 | (1.4) | 4000 | 44 | (0.2) | 12.9 | 926 |
| Total: | 63 | 5400 | (8.6) | 25000 | 250 | (0.4) | 4.6 | 153 |

| Upper body part oxygen consumption | | | |
|---|---|---|---|
| Brain Mass (g) | 1,400 | | |
| Upper Body Muscle Mass (g) | 2,000 | | |
| O₂ (mL/g hemoglobin) | 1.34 | | |
| Hemoglobin (g/L) | 110 | O₂ Content (mL/L blood) | 147 |
| O₂ Saturation Arterial (%) as seen in HO patients | 92 | | |
| O₂ Saturation Venous (%) as seen in HO patients | 61 | Arterio-Venous Oxygen Saturation Difference (%) | 31 |
| Cardiac Output (CO) (mL/min) | 5,000 | | |
| Frac. CO to Upper Body | 0.28 | Upper Body Blood Flow (mL/min) | 1,417 |
| Average Brain Blood Flow (mL/min) | 1,125 | O₂ Delivery Upper Body (mL/min) | 192 |
| Upper Body Muscle Blood Flow (mL/min) | 54 | O₂ Venous Backflow in Superior Caval Vein (mL/min) | 127 |
| Upper Body Skin Blood Flow (mL/min) | 124 | Upper Body O₂ Consumption Calculated Based on Arterio-Venous Difference and Upper Body Blood Flow (mL/min) | 65 |
| Upper Body Residual Blood Flow (mL/min) | 113 | | |
| Sum Upper Body Blood Flow (mL/min) | 1,417 | | |
| | | UB O₂ Consumption Computed Based on Tissue Masses and Blood Flows (mL/min) | 64 |
| Brain O₂ Use (mL/100 g) | 3.5 | | |
| Muscle O₂ Use at Rest (mL/100 g) | 0.20 | | |
| Brain O₂ Use (mL/brain) | 49 | | |
| Muscle O₂ Use (mL/muscle) | 4 | | |
| UB Skin O₂ Consumption (mL/min) | 4 | | |
| Rest O₂ Consumption (mL/min) | 7 | | |

TECHNIQUES FOR NON-INVASIVE DETERMINATION OF ESTIMATED CARDIAC OUTPUT DURING DIALYSIS TREATMENT

TECHNICAL FIELD

Embodiments herein generally relate to processes and apparatuses configured to determine an estimate of cardiac output during a dialysis process, and, in particular, to non-invasive techniques for determining an estimate of cardiac output for an upper body portion of a dialysis patient.

BACKGROUND

Cardiac output is a measure of the effectiveness of the heart at circulating blood through the circulatory system. An abnormal cardiac output is a typical indicator of cardiovascular disease. The mortality rate of hemodialysis (HD) patients is elevated compared to the normal population, and a primary cause of mortality for that patient group includes cardiovascular disease (CVD). In addition, cardiac output CO may change during HD treatment, with a drop in cardiac output correlating with poor patient outcomes.

Accordingly, determining an estimate of cardiac output during an HD treatment may provide an important indicator of patient mortality. However, conventional processes for directly determining cardiac output may be invasive, time consuming, and/or labor intensive. For example, a standard indicator dye technique involves venous injection of indicator dyes and measurement of blood samples to measure the concentration of dye in the blood. In another example, a thermodilution technique involves injection of a thermal indicator into the circulatory system (for instance, in the right side of the heart) and detecting a temperature change as the thermal indicator moves through the circulatory system (for instance, at the left side of the heart). In addition, attempts at estimating cardiac output, such as using related or surrogate values associated with patient blood flow, have been shown in circumstances to be ineffective and inaccurate.

Accordingly, accurate and efficient determination of cardiac output during dialysis may facilitate safe and more proactive dialysis treatment and improved patient health. It is with these considerations in mind that the present disclosure may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with various embodiments of the present disclosure is an apparatus that may include at least one memory and logic coupled to the at least one memory. The logic may operate to determine an upper body oxygen consumption for a patient, determine, during a dialysis process a hemoglobin concentration and a venous oxygen saturation measured via an optical blood monitor operably coupled to an extracorporeal circuit of a dialysis system performing the dialysis process, an arterial oxygen saturation measured via a pulse oximeter operably coupled to the patient, an arterial-venous oxygen content difference based on the arterial oxygen saturation and the venous oxygen saturation, and an upper body blood flow (UBBF or UBBF rate) as (the upper body oxygen consumption)/(the arterial-venous oxygen content difference), and determine a treatment recommendation based on the UBBF. In some embodiments, venous oxygen saturation may be or may include central-venous oxygen saturation, for example, in the vena cava superior or the right atrium (for instance, such that the oxygen saturation is indicative of the oxygen saturation of the upper body of a patient).

In some embodiments of the apparatus, the logic may operate to perform the dialysis process based on the treatment recommendation. In various embodiments of the apparatus, the upper body oxygen consumption may include a sum of oxygen consumption of upper body tissues, that may include a brain oxygen consumption, a heart oxygen consumption, a skeletal muscle oxygen consumption, or a skin oxygen consumption, or any combination thereof. In some embodiments of the apparatus, the treatment recommendation may include at least one change in a dialysate temperature, an ultrafiltration rate, an ultrafiltration goal, or a process duration. In various embodiments of the apparatus, the arterial-venous oxygen content difference may be determined based on a difference between an arterial blood oxygen content and a venous blood oxygen content. In exemplary embodiments of the apparatus, the patient may have a central venous catheter (CVC) access. In some embodiments of the apparatus, the treatment recommendation may be configured to facilitate an improved morbidity and/or an improved mortality of the patient.

In some embodiments of the apparatus, the treatment recommendation may include an adjustment to a parameter (for instance, an adjustment parameter) of the dialysis process. In various embodiments of the apparatus, the adjustment parameter may include at least one of a dialysate temperature, an ultrafiltration rate, an ultrafiltration goal, or a process duration. In exemplary embodiments of the apparatus, the logic may operate to present adjustment information to a user indicating the adjustment parameter. In some embodiments of the apparatus, the logic may operate to automatically adjust the dialysis process based on the adjustment parameter.

In accordance with various embodiments of the present disclosure is a method of performing dialysis on a patient via a dialysis system. The method may include determining an upper body oxygen consumption for the patient, determining, during a dialysis process a hemoglobin concentration and a venous oxygen saturation measured via an optical blood monitor operably coupled to an extracorporeal circuit of a dialysis system performing the dialysis process, an arterial oxygen saturation measured via a pulse oximeter operably coupled to the patient, an arterial-venous oxygen content difference based on the arterial oxygen saturation and the venous oxygen saturation, and an upper body blood flow (UBBF) as (the upper body oxygen consumption)/(the arterial-venous oxygen content difference), and determining a treatment recommendation based on the UBBF.

In some embodiments of the method, the method may include performing the dialysis process based on the treatment recommendation. In various embodiments of the method, the upper body oxygen consumption may include a sum of oxygen consumption of upper body tissues, that may include a brain oxygen consumption, a heart oxygen consumption, a skeletal muscle oxygen consumption, or a skin oxygen consumption, or any combination thereof. In some embodiments of the method, the treatment recommendation may include at least one change in an ultrafiltration rate, an ultrafiltration goal, or a process duration. In various embodiments of the method, the arterial-venous oxygen content difference may be determined based on a difference between an arterial blood oxygen content and a venous blood oxygen content. In exemplary embodiments of the method, the treatment recommendation may be configured to facilitate an improved morbidity and/or an improved mortality of the patient.

In some embodiments of the method, the treatment recommendation may include an adjustment to one or more (adjustment) parameter(s) of the dialysis process. In various embodiments of the method, the adjustment parameter may include at least one of an ultrafiltration rate, an ultrafiltration goal, or a process duration. In exemplary embodiments of the method, the method may include presenting adjustment information to a user indicating the adjustment parameter. In some embodiments of the method, the method may include automatically adjusting the dialysis process based on the adjustment parameter.

In accordance with various embodiments of the present disclosure is a dialysis system configured to perform a dialysis process on a patient. The dialysis system may include an extracorporeal circuit operably coupled to the patient, an optical blood monitor operably coupled to the extracorporeal circuit, a pulse oximeter operably coupled to the patient, at least one processor, and a memory coupled to the at least one processor. The memory may include instructions that, when executed by the at least one processor, cause the at least one processor to determine an upper body oxygen consumption for the patient, determine, during the dialysis process, a hemoglobin concentration and a venous oxygen saturation measured via the optical blood monitor, an arterial oxygen saturation measured via the pulse oximeter, an arterial-venous oxygen content difference based on the arterial oxygen saturation and the venous oxygen saturation, and an upper body blood flow (UBBF) as (the upper body oxygen consumption)/(the arterial-venous oxygen content difference), and determine a treatment recommendation based on the UBBF.

In some embodiments of the dialysis system, the instructions, when executed by the at least one processor, may cause the at least one processor to perform the dialysis process based on the treatment recommendation. In various embodiments of the dialysis system, the upper body oxygen consumption may include a sum of oxygen consumption of upper body tissues, that may include a brain oxygen consumption, a heart oxygen consumption, a skeletal muscle oxygen consumption, or a skin oxygen consumption, or any combination thereof. In some embodiments of the dialysis system, the treatment recommendation may include at least one change in an ultrafiltration rate, an ultrafiltration goal, or a process duration. In various embodiments of the dialysis system, the arterial-venous oxygen content difference may be determined based on a difference between an arterial blood oxygen content and a venous blood oxygen content. In exemplary embodiments of the dialysis system, the patient may have a central venous catheter (CVC) access. In some embodiments of the dialysis system, the treatment recommendation may be configured to facilitate an improved morbidity and/or an improved mortality of the patient.

DETAILED DESCRIPTION

Various embodiments may generally be directed toward systems, methods, and/or apparatus for determining cardiac output (CO) in patients undergoing dialysis treatment. In some embodiments, a cardiac output analysis process may generate an estimated CO (eCO). In various embodiments, the eCO may be an upper body blood flow (UBBF or UBBF rate) value. For example, the UBBF value may be determined during a hemodialysis (HD) process for patients with a central venous catheter (CVC) based on the oxygen consumption of upper body organs (i.e., a sum of oxygen consumption in upper body tissues) and a measurement of central venous oxygen saturation ($S_{cv}O_2$) and peripheral arterial oxygen saturation ($S_aO_2$) detected during a dialysis process. Although examples in the present disclosure may describe processes for patients with a CVC, for instance, for determining oxygen saturation levels (for example, $S_{cv}O_2$, $S_vO_2$, and/or the like), embodiments are not so limited, as embodiments may operate using non-invasive processes that do not require a patient to have a CVC. In one example, for instance, $S_{cv}O_2$ can be approximated by measurements of $S_vO2$ in the internal jugular vein using near infrared spectroscopy, for instance, the same or similar to the methods described in Ruan et al. "Monitoring Tissue Blood Oxygen Saturation in the Internal Jugular Venous Area Using Near Infrared Spectroscopy," Genet Mol Res 31; 14(1):2920-8 (March 2015), which is incorporated by reference in this Detailed Description as if fully set forth herein. Other non-invasive methods may also be used. In various embodiments, the UBBF value may be determined during dialysis continuously, periodically (e.g., at time intervals), based on an event (e.g., based on a patient vital or other physiological parameter), and/or the like. In some embodiments, $S_{cv}O_2$ may be used to determine a venous oxygen content ($C_v$) and $S_aO_2$ may be used to determine an arterial oxygen content ($C_a$). In exemplary embodiments, UBBF may be determined as (sum of oxygen consumption in upper body tissues)/(arterio-venous difference in oxygen content). In some embodiments, the term "upper body" may refer to all tissues and organs with venous blood drainage into the superior caval vein.

In one embodiment, for example, in HD patients with a CVC (or in patients without a CVC through non-invasive methods), $S_{cv}O_2$ and hematocrit concentration may be measured by an optical blood monitor operably coupled to an extracorporeal circuit of an HD dialysis system while performing HD on a patient. $S_{cv}O_2$ may be used to calculate $C_v$ and the hematocrit concentration may be used to determine a hemoglobin (Hgb) concentration. In parallel, $S_aO_2$ may be measured by a pulse-oximeter device, which may be used to calculate $C_a$. Accordingly, $S_{cv}O_2$, $S_aO_2$, and Hgb changes during HD can be measured during a dialysis process, which may be used to calculate UBBF during HD, for instance, continuously and/or periodically.

In some embodiments, hemoglobin concentration may be determined from measured hematocrit values. For example, hemoglobin concentration (for instance, in units of g/dL) may be equal to hematocrit (% packed cell volume (PCV))× about 0.3 (for instance, 0.34). In another example, hemoglobin concentration (for instance, in units of g/dL) may be equal to hematocrit (decimal fraction)×about 30 (for instance, 34). Other methods for determining hemoglobin concentration from hematocrit may also be used. Embodiments are not limited in this context.

In some embodiments, the optical blood monitor may be or may include a hematocrit measuring device such as a Crit-Line® Monitor (CLM), available from Fresenius Medical Care Waltham, Mass., United States of America. In general, a CLM may be an inline monitor (for instance, operably coupled to the extracorporeal circuit used for performing HD) operative to measure hematocrit, oxygen saturation, and/or changes in blood volume during dialysis treatment. Although a CLM may be used in some examples, embodiments are not so limited, as any technique, device, process, and/or the like for measuring and/or predicting hematocrit capable of operating according to some embodiments is contemplated herein. In some embodiments, the pulse oximeter may be operably coupled to the optical blood monitor (for instance, a CLM) to implement a single blood characteristic measurement device capable of measuring $S_{cv}O_2$, $S_aO_2$, and Hgb changes, and, therefore, UBBF, during HD. Although a pulse-oximeter may be used, for example, to determine oxygen saturation in some examples, embodiments are not so limited as other devices, methods, and/or the like may be used to measure oxygen saturation (for instance, invasively in patients with a cannulated artery in a hospital/intensive care unit (ICU) setting).

As discussed above, CO changes during HD treatment have been demonstrated by various patient studies. In general, a drop in CO correlates with poor patient outcomes. CO may be determined via certain direct measurements (for instance, thermodilution and indicator dye techniques) and/or calculated applying Fick's principle according to the following Equation (1):

CO=oxygen consumption ($VO_2$)/(Arterial oxygen content−Venous oxygen content).

Whole body $VO_2$ can be estimated by various methods, such as the formula 3 ml $O_2$/kg, the Dehmer formula, the LaFarge formula, and/or the Bergstra formula. In some embodiments, Arterial ($C_a$) and venous ($C_v$) oxygen content may be calculated based on $SaO_2$ and $ScvO_2$, respectively, measured according to some embodiments. For example, arterial oxygen content may be determined based on the following Equation (2):

$C_aO_2$=(1.34×Hgb×$S_aO_2$)+($P_aO_2$×0.0031), where $P_aO_2$ may be measured with arterial blood gas, or estimated as 100 torr (or other similar estimate). In another example, venous oxygen content may be determined based on the following Equation (3):

$C_vO_2$=(1.34×Hgb×$S_{cv}O_2$)+($P_vO_2$×0.0031), where PvO2 may be measured with venous blood gas, or estimated as 35 torr.

Upper body oxygen consumption (or upper body oxygen consumption rate) can be calculated by multiplying the respective tissue weights with the tissue-specific oxygen consumption per unit of tissue mass, for example, according to the following Equation (4):

tissue mass (g)×(O2 consumption/100 g mass/min)/100.

For example, the brain oxygen consumption can be calculated as 1400 [g brain mass] *3.5 [mL oxygen consumption/100 g brain mass/min]/100. In another example, the arm muscle oxygen consumption at rest can be calculated as 2000 [g arm muscle mass] *0.2 [mL oxygen consumption/100 g muscle mass/min]/100.

The sum of the oxygen consumption (or oxygen consumption rate) by tissues in the upper body part is the total upper body part oxygen consumption. At rest, this value is assumed to be stable. Blood oxygen content in mL oxygen per dL blood can be calculated by the following Equation (5):

Hemoglobin (Hgb) concentration [g/dL]*Oxygen Saturation [%]*1.34/100, where the constant 1.34 reflects that each gram of Hgb can carry up to 1.34 mL of oxygen.

In some embodiments, one or more physiological measurement devices, such as a CLM, may measure oxygen saturation and hematocrit (for conversion to Hgb concentration), which may be used to determine blood oxygen content. Using CLM (or other measurement device(s)) in HD patients with a CVC as vascular access, a CO estimation process according to some embodiments may estimate the fraction of CO that perfuses the upper body parts, most prominently the brain, arm muscles, and the skin by applying a modification of the Fick equation, where CO is replaced by upper body blood flow (UBBF). In some embodiments, UBBF may be determined according to the following Equation (6):

UBBF=sum of oxygen consumption in upper body tissues/arterio-venous difference in oxygen content.

UBBF determined according to some embodiments may operate as an efficient, effective, and accurate estimate of CO of a patient undergoing HD. Treatment modifications in order to prevent CO drop could be applied to high risk patients detected by processes according to some embodiments. Improvement in cardiovascular related morbidity and mortality may be provided to patients using a CO estimation process according to some embodiments for patients.

Therefore, CO analysis processes according to some embodiments may provide multiple technological advantages and technical features over conventional systems, including improvements to computing technology. One non-limiting example of a technological advantage may include determining an accurate CO estimate in the form of UBBF continuously and/or periodically during a dialysis treatment. Accordingly, CO for an HD patient may be monitored during an HD treatment session providing real-time or substantially real-time insight into patient cardiac health during dialysis. Another non-limiting example of a technological advantage may include the ability of a healthcare professional and/or dialysis device to receive a treatment recommendation based on an accurate CO estimate in the form of UBBF continuously during a dialysis treatment. In this manner, HD treatment for the patient may be adjusted in real-time or substantially real-time in response to changes in CO for the patient. Accordingly, some embodiments may determine an estimated CO in the form of UBBF for the practical application of determining a treatment recommendation for future HD treatments and/or to change the course of an active HD treatment (for example, by changing filtration rates, filtration times, medicament dosages, and/or the like). At least one potential disadvantage with conventional HD computing technology is that it is not able to manage patients based on real-time, continuously- or periodically-measured CO information. Accordingly, some embodiments may provide improvements in computing technology by facilitating real-time changes to an HD treatment based on CO information in the form of UBBF. In addition, some embodiments may provide a practical application of CO determinations, including CO estimates, UBBF, and/or the like. Non-limiting practical applications may include using CO determinations according to some embodiments to administer dialysis and improving dialysis patient morbidity and/or mortality. Other technological advantages, improvements, and/or practical applications are provided by embodiments described in the present disclosure. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

Figure 1:
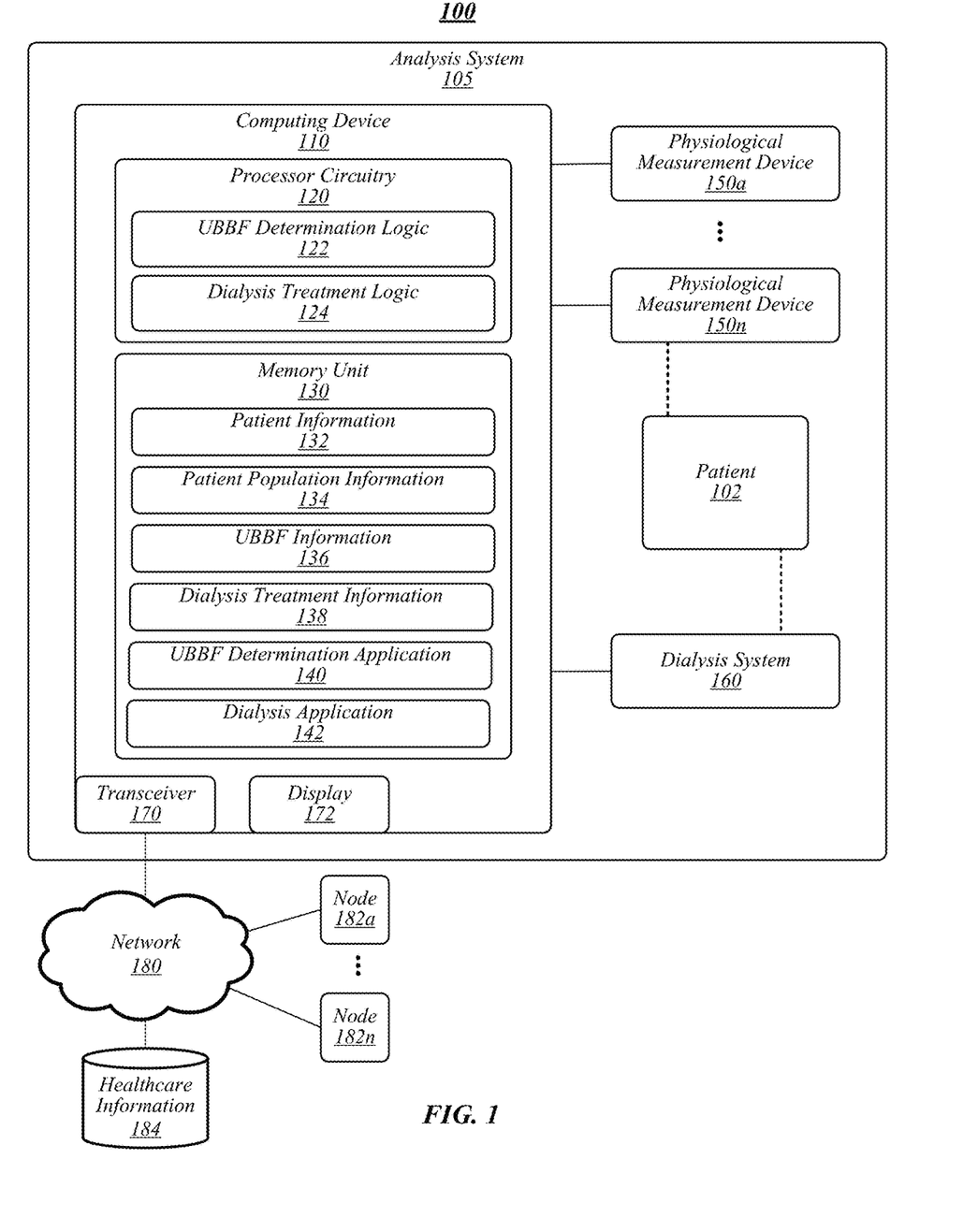
FIG. 1 illustrates an embodiment of a first operating environment.

FIG. 1 illustrates an example of an operating environment 100 that may be representative of some embodiments. Operating environment 100 may include an analysis system 105 operative to perform a CO estimation process according to some embodiments. As shown in FIG. 1, analysis system 105 may include computing device 110 communicatively coupled to one or more physiological measurement devices 150a-n and/or dialysis device 160 (see, for example, FIG. 5), or otherwise configured to receive and store data therefrom. Physiological measurement devices 150a-n and/or dialysis system 160 may operate to provide data and/or other signals to a location on a network 150 (for instance, a cloud computing environment), such as nodes 182a-n, healthcare information database 184, and/or the like, accessible to computing device 110. In some embodiments, computing device 110 may be operative to control, monitor, manage, or otherwise process various operational aspects of physiological measurement devices 150a-n and/or dialysis system 160. In some embodiments, computing device 110 may be or may include a stand-alone computing device, such as a personal computer (PC), server, tablet computing device, cloud computing device, smartphone, tablet computing device, and/or the like. In some embodiments, computing device 110 may be an embedded computing device in one or more of physiological measurement devices 150a-n and/or medical devices 160a-n.

As shown in FIG. 1, computing device 110 may include processing circuitry 120, a memory unit 130, a transceiver 170, and/or a display 172. Processing circuitry 120 may be communicatively coupled to memory unit 130, transceiver 170, and/or display 172.

Processing circuitry 120 may include and/or may access various logic for performing processes according to some embodiments. For instance, processing circuitry 120 may include and/or may access UBBF determination logic 122 and/or dialysis treatment logic 124. Processing circuitry 120, UBBF determination logic 122, and/or dialysis treatment logic 124, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1400 (FIG. 14). For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although UBBF determination logic 122 and dialysis treatment logic 124 is depicted in FIG. 1 as being within processing circuitry 120, embodiments are not so limited. For example, UBBF determination logic 122 and/or dialysis treatment logic 124 may be located within an accelerator, a processor core, an interface, an individual processor die, implemented entirely as a software application (for instance, UBBF determination application 140 and/or dialysis application 142) and/or the like. In addition, analysis system 105 may include a plurality of computing devices 110 as a single computing device 110 is depicted in FIG. 1 to simplify the figure. For example, one computing device 110 may be configured to perform a CO estimation process according to some embodiments (and include UBBF determination logic 122 and/or UBBF determination application 140), while a second computing device 110 may be configured to perform a dialysis process (for instance, as a dialysis controller device (see, for example, FIG. 5) (and include dialysis treatment logic 124 and/or dialysis application 142).

In some embodiments, physiological measurement devices 150a-n may include various devices operative to measure physiological characteristics of a patient. Non-limiting examples of physiological devices 150a-n may include an oxygen concentration measurement device, hematocrit measurement device (for instance, a CLM), hemoglobin measurement device, an optical blood measurement device, a pulse oximeter, and/or the like. Although a hematocrit measurement device (for instance, a CLM) may be used as an illustrative physiological measurement device 150a-n, embodiments are not so limited, as physiological measurement devices 150a-n may include any type of device capable of measuring physiological information of a patient.

In some embodiments, physiological measurement devices 150a-n may be operably coupled in-line with an extracorporeal circuit connected to patient 102 for use by dialysis system 160 to perform a dialysis process (for instance, an HD process). In some embodiments, physiological measurement device may include a single measurement device capable of measuring $S_{cv}O_2$, $S_aO_2$, and/or Hgb (measured hematocrit) continuously, semi-continuously, periodically, event-based, and/or the like during an HD treatment.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store patient information 132, patient population information 134, UBBF information 136, dialysis treatment information 138, a UBBF determination application 140, and/or a dialysis application 142. In some embodiments, patient information 132 may generally include information associated with one or more patients, such as patient 102, undergoing dialysis treatment via dialysis system 160. Patient information 132 may include medical records and/or physical information of patient, such as height, weight, gender, dialysis treatment prescription information, and/or the like.

Figure 2:
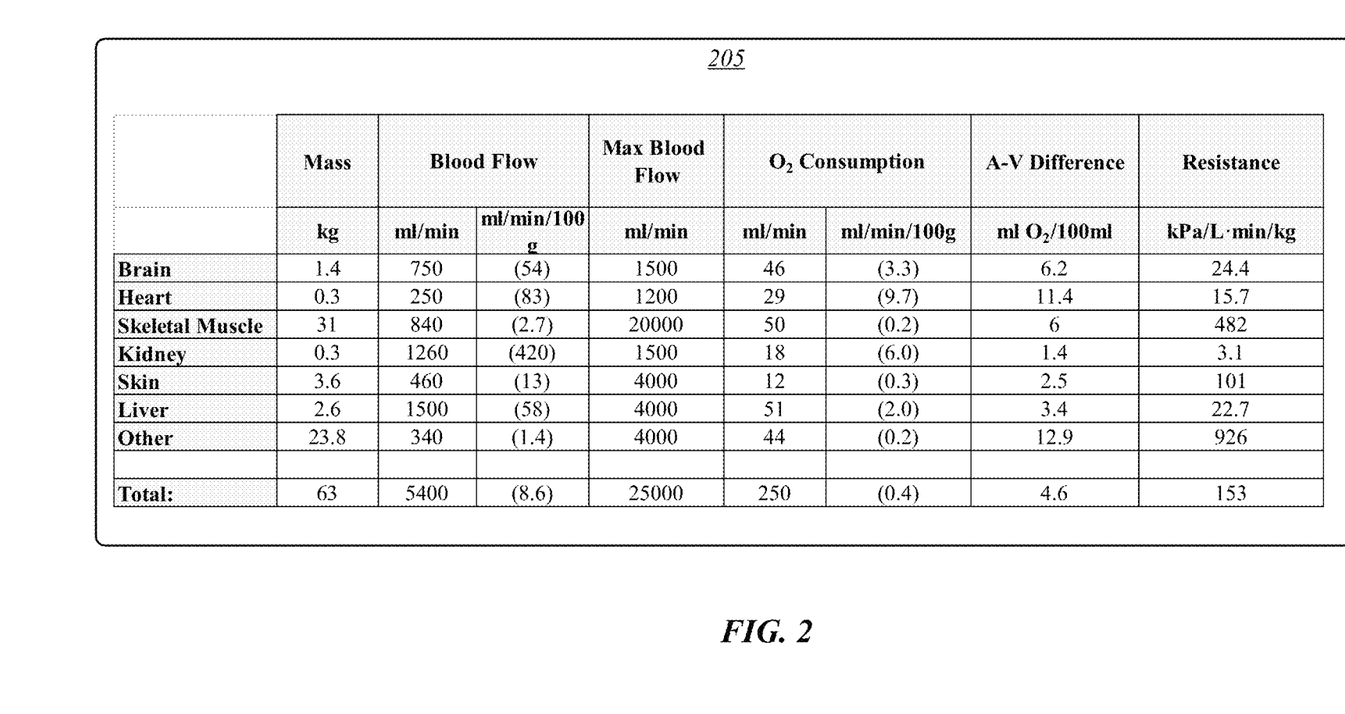
FIG. 2 illustrates a table of physiological values for upper body tissues according to some embodiments.

Patient population information 134 may include physiological information for various populations of patients that are undergoing dialysis treatment. Non-limiting examples of population information 134 may include $S_{cv}O_2$, $S_aO_2$, Hgb, tissue characteristics (for example, mass, blood flow, oxygen consumption, arterio-venous (A-V) difference; see, for instance, FIG. 2), UBBF estimations, CO information, historical information thereof, dynamic information during one or more dialysis treatments, and/or the like. FIG. 2 illustrates a table of physiological values for body organs and tissues according to some embodiments. In some embodiments, population information 134 may be used for certain values used to determine UBBF information 136, such as a UBBF value for patient 102 undergoing HD as described in more detail below. As shown in FIG. 2, values for mass, blood flow, maximum blood flow, oxygen consumption, A-V difference, and resistance may be determined based on a population of patients.

In some embodiments, UBBF determination application 140, for example, via UBBF determination logic 122, may use patient information 132 and/or patient population information 134 to determine UBBF information 136. In various embodiments, UBBF information 136 may be a UBBF value for patient 102 undergoing HD. In some embodiments, UBBF information 136 may be or may include historical UBBF information for a patient, for instance, dynamic changes in UBBF during a treatment, a UBBF trajectory or other historical measurement over a course of treatments, and/or the like.

In some embodiments, UBBF determination application 140 may determine UBBF based on Equation (6), in particular:

UBBF=sum of oxygen consumption in upper body tissues/$A-V$ difference in oxygen content.

The sum of oxygen consumption in upper body tissues (upper body oxygen consumption) may be determined based on one or more upper body tissues, such as the brain, heart, skeletal muscle, skin, and/or the like (see, for example, FIG. 2). The A–V difference in oxygen content (A–V oxygen content difference) may be determined based on $C_a$-$C_v$, where $C_a$ is determined based on $S_aO_2$ and $C_v$ is determined based on $S_{cv}O_2$ according to some embodiments.

Figure 3:
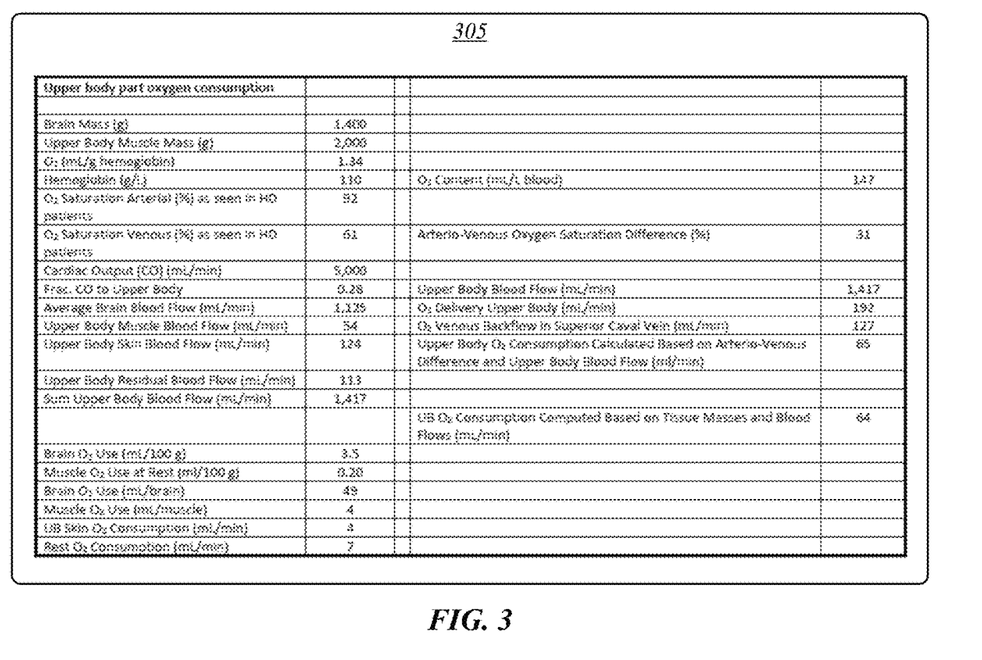
FIG. 3 illustrates a table of oxygen consumption information for upper body tissues according to some embodiments.

FIG. 3 illustrates a table of oxygen consumption information for upper body tissues according to some embodiments. Comparing upper body oxygen consumption calculated based on population average values of $S_{cv}O_2$ and $S_aO_2$ obtained in HD patients and literature data of CO and on one hand (for instance, as patient population information 134), and organ specific oxygen uptake rates on the other hand, demonstrates that results that are in good agreement (65 vs 64 mL/min as shown in Table 305 of FIG. 3), demonstrating the effectiveness and accuracy of CO estimation processes according to some embodiments.

In some embodiments, UBBF determination application 140, for example, via UBBF determination logic 122, may generate dialysis treatment information 138, for example, in the form of a diagnosis, treatment recommendation, treatment adjustment, and/or the like. For example, treatment recommendations, adjustments, or modifications may be determined by UBBF determination application 140 based on UBBF information 136 (for example, a UBBF value serving as an estimate/proxy of CO), and/or historical UBBF information 136, for example, indicating trends or other dynamic changes during one or more dialysis treatment recommendations. Non-limiting examples of treatment recommendations may include aborting a dialysis treatment, changing a dialysis treatment (adjustment) parameter (for instance, an ultrafiltration rate (UFR), ultrafiltration goal (UFG)), changing a medicament dosage (for instance, a diuretic, a calcium channel blocker, and/or the like), and/or the like. In some embodiments, the treatment recommendation or adjustment may be communicated to patient 102 and/or a healthcare provider of patient 102, for instance, by being presented on display 172 and/or via a communication message (for instance, email, SMS message, and/or the like). In various embodiments, a treatment recommendation or adjustment may be implemented automatically, for example, via dialysis application. In other embodiments, a treatment recommendation or adjustment may be displayed for a final decision and/or implementation by a healthcare professional.

In some embodiments, dialysis application 142, for example, via dialysis treatment logic 124, may operate to manage or otherwise control at least a portion of a dialysis process of dialysis system 160. For instance, dialysis application 142 may include software for controlling an HD process for patient 102, for example, based on a prescription with specific (adjustment) parameters, such as UFR, UFG, medicament dosage, and/or the like. In various embodiments, dialysis application 142, for example, via dialysis treatment logic 124, may change a dialysis treatment based on a treatment recommendation generated based on UBBF information. For example, dialysis application 142 may abort a dialysis process, change a UFR, change a UFG, change a medicament dosage, and/or the like based on a patient CO as determined based on UBBF.

In some embodiments, UBBF determination application 140 and/or dialysis application 142 may include application programming interfaces (APIs) and/or graphical user interfaces (GUIs) to read, write, and/or otherwise access UBBF information 136 and/or dialysis treatment information 138, such as via display 172 and/or corresponding displays of physiological measurement devices 150*a-n*, dialysis system, nodes 182*a-n*, healthcare information 184, web interfaces, mobile application ("mobile applications," "mobile apps," or "apps"), and/or the like. In this manner, in some embodiments, an operator may search, visualize, read, add to, or otherwise access patient records, UBBF information 136, and/or dialysis treatment information 138.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 4:
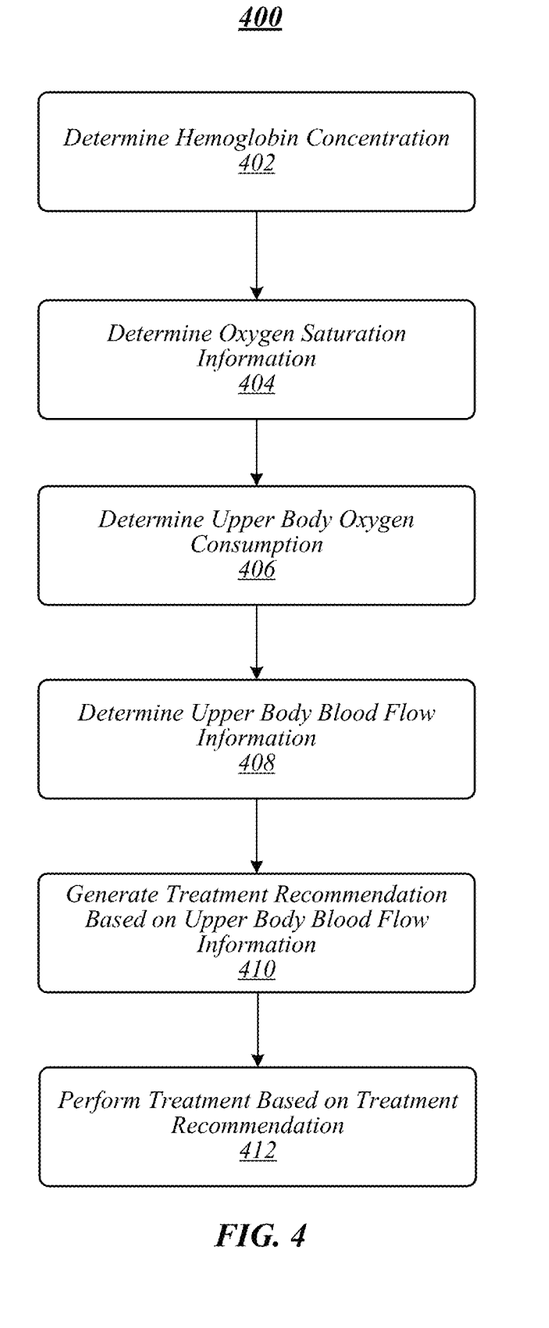
FIG. 4 illustrates an embodiment of a logic flow.

FIG. 4 illustrates an embodiment of a logic flow 400. Logic flow 400 may be representative of some or all of the operations executed by one or more embodiments described herein, such as computing device 110. In some embodiments, logic flow 400 may be representative of some or all of the operations of CO estimation process according to some embodiments.

At block 402, logic flow 400 may determine an Hgb concentration. For example, a physiological measurement device 150*a-n* may include a CLM configured to measure patient hematocrit, which may be used to determine an Hgb concentration. Logic flow 400 may determine oxygen saturation information at block 404. For example, one or more physiological measurement devices 150*a-n* may measure $S_aO_2$ and $S_{cv}O_2$ of patient 102. UBBF determination application 140 may determine $C_a$ and $C_v$ based on $S_aO_2$ and $S_{cv}O_2$, respectively (see, for example, Equations (2) and (3) and/or FIG. 3). At block 406, logic flow 400 may determine an upper body oxygen consumption. For example, UBBF determination application 140 may determine upper body oxygen consumption as the sum of the oxygen consumption by tissues in the upper body portion of patient 102 (see, for example, FIG. 2 and/or FIG. 3). Logic flow 400 may determine upper body blood flow information at block 408. For example, UBBF determination application 140 may determine a UBBF value for patient 102 at one or more measurement intervals during an HD process. The UBBF value may be determined according to Equation (6).

At block 410, logic flow 400 may generate a treatment recommendation based on UBBF. For example, UBBF determination application 140 may generate a treatment recommendation for a current and/or future HD treatment of patient based on the UBBF value determined in block 408. In general, the treatment recommendation may be generated to maintain or achieve a healthy CO (as much as possible) for patient 102. For example, a treatment recommendation may include a modification to a UFR and/or a UFG during an active HD treatment. In some embodiments, the treatment recommendation may be communicated to the patient and/or healthcare professional administering the HD treatment. In various embodiments, the treatment recommendation may be communicated to dialysis system 160 to modify a current treatment. Logic flow 400 may perform a treatment based on the treatment recommendation at block 412. For example, dialysis application 142 may determine or receive a treatment recommendation and may control dialysis system 160 in order to achieve the treatment recommendation. For example, dialysis application 142 may cause a change in a UFR for patient 102 via dialysis system. In some embodiments, performance of a dialysis treatment process at block 412 may include continuing and/or altering an active dialysis treatment modified according to the treatment recommendation.

Although blocks of logic flow 400 are depicted in FIG. 4 as occurring in a certain order, embodiments are not so limited. For example, blocks 402, 404, and/or 406 may occur concurrently or semi-concurrently for providing information for determining the UBBF information in block 408.

Figure 5:
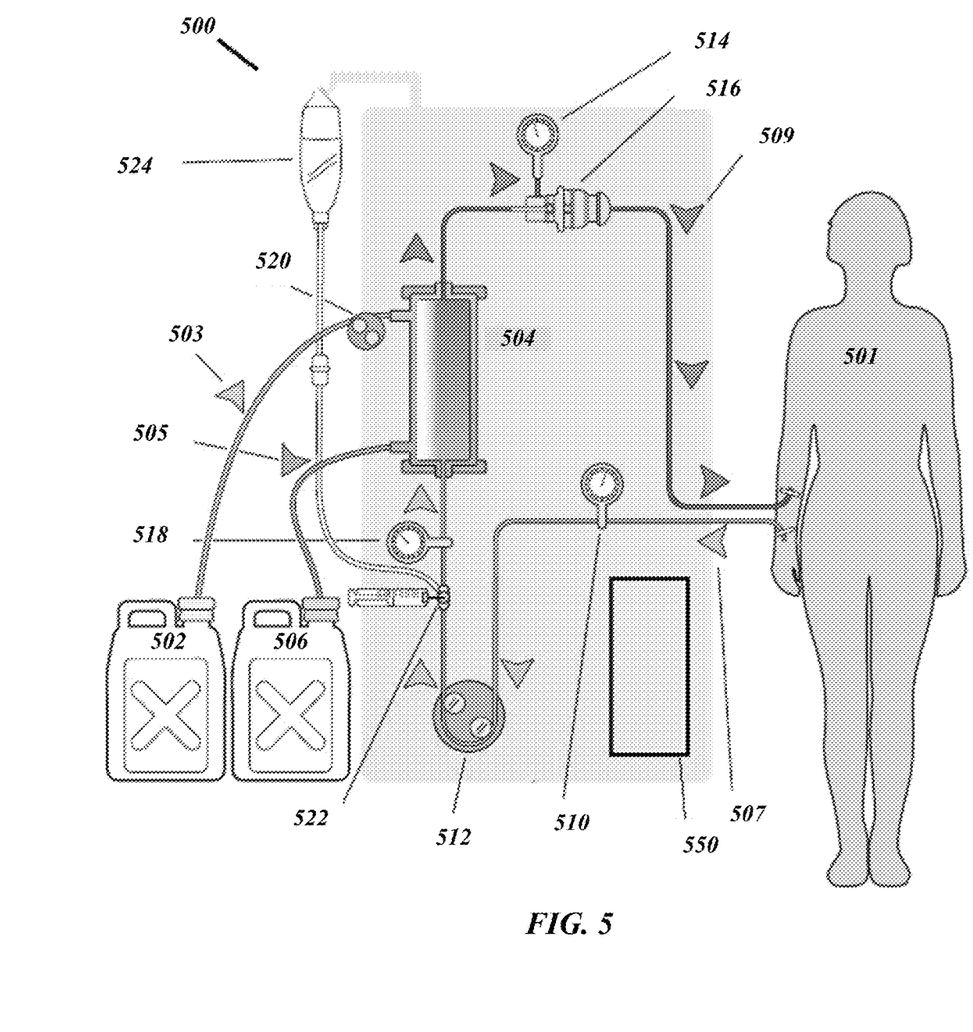
FIG. 5 illustrates an example hemodialysis system.

FIG. 5 illustrates a diagram of an exemplary embodiment of a dialysis system 500 in accordance with the present disclosure. Dialysis system 500 may be configured to provide hemodialysis (HD) treatment for a patient 501. Fluid reservoir 502 may deliver fresh dialysate to a dialyzer 504 via tubing 503, and reservoir 506 may receive spent dialysate once it has passed through dialyzer 504 via tubing 505. A hemodialysis operation may filter particulates and/or contaminates from a patient's blood through a patient external filtration device, for example, a dialyzer 504. As the dialysate is passed through dialyzer 504, unfiltered patient blood is also passed into dialyzer 504 via tubing 507 and filtered blood is returned to patient 501 via tubing 509. Arterial pressure may be monitored via pressure sensor 510, inflow pressure monitored via sensor 518, and venous pressure monitored via pressure sensor 514. An air trap and detector 516 may ensure that air is not introduced into patient blood as it is filtered and returned to patient 501. The flow of blood 507 and the flow of dialysate may be controlled via respective pumps, including a blood pump 512 and a fluid pump 520. Heparin 522, a blood thinner, may be used in conjunction with saline 524 to ensure blood clots do not form or occlude blood flow through the system.

In some embodiments, dialysis system 500 may include a controller 550, which may be similar to computing device 110 and/or components thereof (for instance, processor circuitry 50). Controller 550 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. In various embodiments, controller may receive and/or calculate hemoglobin concentrations, AR measurements, flow rates, and/or the like. Controller 550 may also be operatively connected to and/or communicate with additional sensors or sensor systems, devices, and/or the like, although controller 550 may use any of the data available on the patient's biologic functions or other patient parameters. For example, controller 550 may send patient data to computing device 110, healthcare exchange platform 205, and/or integrated care system 305 and/or 405 to determine AR values according to some embodiments. Machine 500 and/or components thereof, such as controller 550, may be operably coupled to a hematocrit measurement device, CLM, hemoglobin concentration measurement device, and/or the like to facilitate processes performed by computing device 110.

Figure 6:
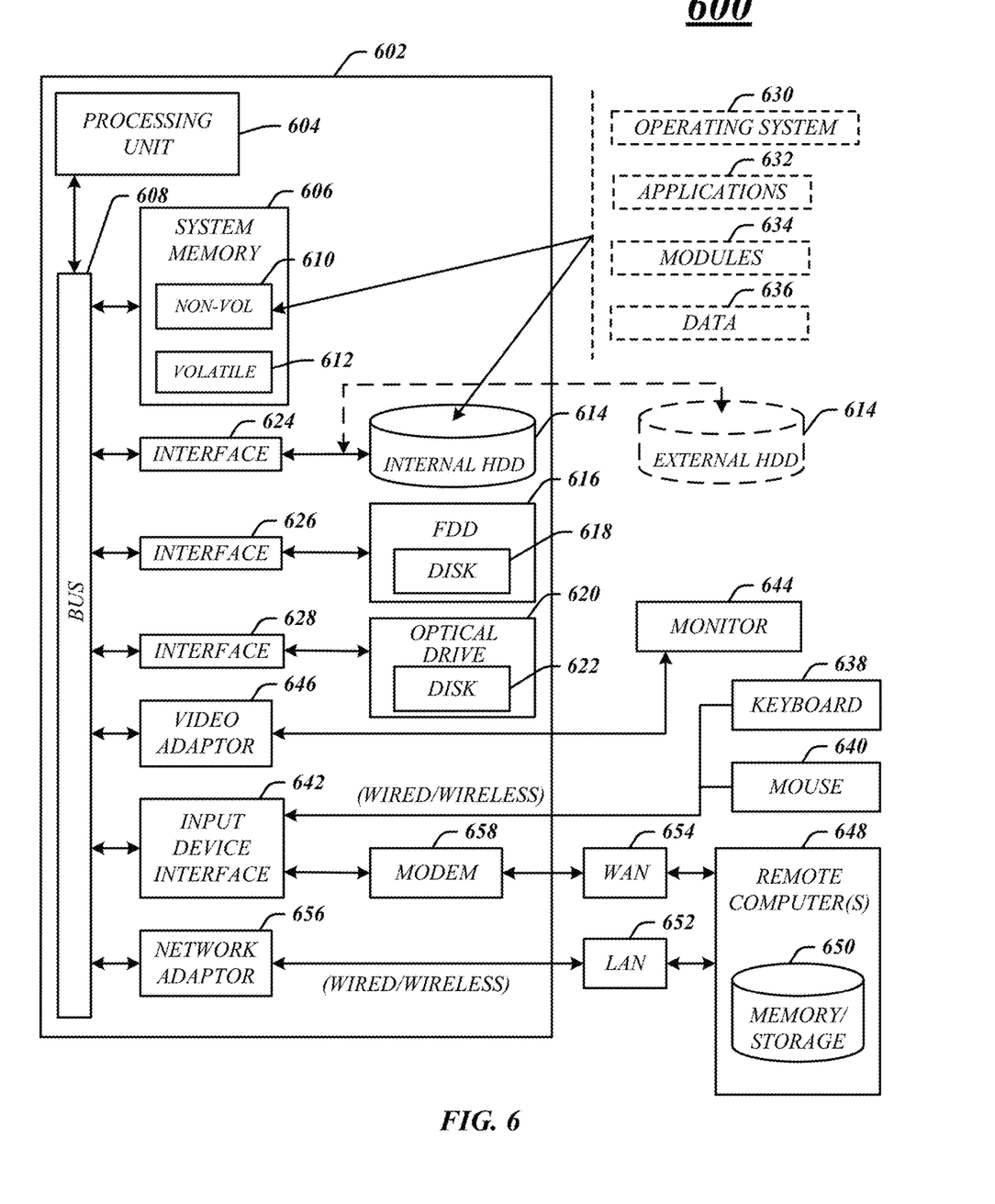
FIG. 6 illustrates an embodiment of a computing architecture.

FIG. 6 illustrates an embodiment of an exemplary computing architecture 600 suitable for implementing various embodiments as previously described. In various embodiments, the computing architecture 600 may comprise or be implemented as part of an electronic device. In some embodiments, the computing architecture 600 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 600. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 600 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 600.

As shown in FIG. 6, the computing architecture 600 comprises a processing unit 604, a system memory 606 and a system bus 606. The processing unit 604 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 604.

The system bus 606 provides an interface for system components including, but not limited to, the system memory 606 to the processing unit 604. The system bus 606 can be any of several types of bus structure that may further interconnect to a memory bus (with or without a memory controller), a peripheral bus, and a local bus using any of a variety of commercially available bus architectures. Interface adapters may connect to the system bus 606 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 606 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 6, the system memory 606 can include non-volatile memory 610 and/or volatile memory 612. A basic input/output system (BIOS) can be stored in the non-volatile memory 610.

The computer 602 may include various types of computer-readable storage media in the form of one or more lower speed memory units, including an internal (or external) hard disk drive (HDD) 614, a magnetic floppy disk drive (FDD) 616 to read from or write to a removable magnetic disk 616, and an optical disk drive 620 to read from or write to a removable optical disk 622 (e.g., a CD-ROM or DVD). The HDD 614, FDD 616 and optical disk drive 620 can be connected to the system bus 606 by a HDD interface 624, an FDD interface 626 and an optical drive interface 626, respectively. The HDD interface 624 for external drive implementations can include at least one or both of Universal Serial Bus (USB) and IEEE 6144 interface technologies.

The drives and associated computer-readable media provide volatile and/or nonvolatile storage of data, data structures, computer-executable instructions, and so forth. For example, a number of program modules can be stored in the drives and memory units 610, 612, including an operating system 630, one or more application programs 632, other program modules 634, and program data 636. In one embodiment, the one or more application programs 632, other program modules 634, and program data 636 can include, for example, the various applications and/or components of computing device 110.

A user can enter commands and information into the computer 602 through one or more wire/wireless input devices, for example, a keyboard 636 and a pointing device, such as a mouse 640. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 604 through an input device interface 642 that is coupled to the system bus 606, but can be connected by other interfaces such as a parallel port, IEEE 694 serial port, a game port, a USB port, an IR interface, and so forth.

A monitor 644 or other type of display device is also connected to the system bus 606 via an interface, such as a video adaptor 646. The monitor 644 may be internal or external to the computer 802. In addition to the monitor 644, a computer typically includes other peripheral output devices, such as speakers, printers, and so forth.

The computer 602 may operate in a networked environment using logical connections via wire and/or wireless communications to one or more remote computers, such as a remote computer 646. The remote computer 646 can be a workstation, a server computer, a router, a personal computer, portable computer, microprocessor-based entertainment appliance, a peer device or other common network node, and typically includes many or all of the elements described relative to the computer 602, although, for purposes of brevity, only a memory/storage device 650 is illustrated. The logical connections depicted include wire/wireless connectivity to a local area network (LAN) 652 and/or larger networks, for example, a wide area network (WAN) 654. Such LAN and WAN networking environments are commonplace in offices and companies, and facilitate enterprise-wide computer networks, such as intranets, all of which may connect to a global communications network, for example, the Internet.

When used in a LAN networking environment, the computer 602 is connected to the LAN 652 through a wire and/or wireless communication network interface or adaptor 656. The adaptor 656 can facilitate wire and/or wireless communications to the LAN 652, which may also include a wireless access point disposed thereon for communicating with the wireless functionality of the adaptor 656.

When used in a WAN networking environment, the computer 602 can include a modem 656, or is connected to a communications server on the WAN 654, or has other means for establishing communications over the WAN 654, such as by way of the Internet. The modem 656, which can be internal or external and a wire and/or wireless device, connects to the system bus 606 via the input device interface 642. In a networked environment, program modules depicted relative to the computer 602, or portions thereof, can be stored in the remote memory/storage device 650. It will be appreciated that the network connections shown are exemplary and other means of establishing a communications link between the computers can be used.

The computer 602 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
at least one memory; and
logic coupled to the at least one memory, the logic to:
determine an upper body oxygen consumption for a patient,
determine during a dialysis process:
a hemoglobin concentration and a venous oxygen saturation measured via an optical blood monitor operably coupled to an extracorporeal circuit of a dialysis system performing the dialysis process, an arterial oxygen saturation measured via a pulse oximeter operably coupled to the patient, an arterial-venous oxygen content difference based on the arterial oxygen saturation and the venous oxygen saturation, and an upper body blood flow (UBBF) as (the upper body oxygen consumption)/(the arterial-venous oxygen content difference), and determine a treatment recommendation based on the UBBF.

2. The apparatus of claim 1, the logic to perform the dialysis process based on the treatment recommendation.

3. The apparatus of claim 1, the treatment recommendation comprising an adjustment to an adjustment parameter of the dialysis process.

4. The apparatus of claim 3, the adjustment parameter comprising at least one of an ultrafiltration rate, an ultrafiltration goal, and a process duration.

5. The apparatus of claim 3, the logic to present adjustment information to a user indicating the adjustment parameter.

6. The apparatus of claim 3, the logic to automatically adjust the dialysis process based on the adjustment parameter.

7. The apparatus of claim 1, the upper body oxygen consumption comprising a sum of oxygen consumption of upper body tissues, the upper body tissues comprising a brain, a heart, skeletal muscle, skin, or any combination thereof.

8. The apparatus of claim 1, the arterial-venous oxygen content difference determined based on a difference between an arterial blood oxygen content and a venous blood oxygen content.

9. The apparatus of claim 1, the treatment recommendation determined to facilitate an improved morbidity of the patient.

10. A method of performing dialysis on a patient via a dialysis system, comprising:

determining an upper body oxygen consumption for the patient;

determining during a dialysis process:

a hemoglobin concentration and a venous oxygen saturation measured via an optical blood monitor operably coupled to an extracorporeal circuit of a dialysis system performing the dialysis process, an arterial oxygen saturation measured via a pulse oximeter operably coupled to the patient, an arterial-venous oxygen content difference based on the arterial oxygen saturation and the venous oxygen saturation, and an upper body blood flow (UBBF) as (the upper body oxygen consumption)/(the arterial-venous oxygen content difference); and determining a treatment recommendation based on the UBBF.

11. The method of claim 10, comprising performing the dialysis process based on the treatment recommendation.

12. The method of claim 10, the treatment recommendation comprising an adjustment to an adjustment parameter of the dialysis process.

13. The method of claim 12, the adjustment parameter comprising at least one of an ultrafiltration rate, an ultrafiltration goal, or a process duration.

14. The method of claim 13, comprising presenting adjustment information to a user indicating the adjustment parameter.

15. The method of claim 12, comprising automatically adjusting the dialysis process based on the adjustment parameter.

16. The method of claim 10, the upper body oxygen consumption comprising a sum of oxygen consumption of upper body tissues, the upper body tissues comprising a brain, a heart, skeletal muscle, skin, or any combination thereof.

17. The method of claim 10, the arterial-venous oxygen content difference determined based on a difference between an arterial blood oxygen content and a venous blood oxygen content.

18. A dialysis system configured to perform a dialysis process on a patient, comprising:

an extracorporeal circuit operably coupled to the patient;

an optical blood monitor operably coupled to the extracorporeal circuit;

a pulse oximeter operably coupled to the patient;

at least one processor; and a memory coupled to the at least one processor, the memory comprising instructions that, when executed by the at least one processor, cause the at least one processor to:

determine an upper body oxygen consumption for the patient;

determine during the dialysis process:

a hemoglobin concentration and a venous oxygen saturation measured via the optical blood monitor, an arterial oxygen saturation measured via the pulse oximeter, an arterial-venous oxygen content difference based on the arterial oxygen saturation and the venous oxygen saturation, and an upper body blood flow (UBBF) as (the upper body oxygen consumption)/(the arterial-venous oxygen content difference); and determine a treatment recommendation based on the UBBF.

19. The dialysis system of claim 18, the instructions, when executed by the at least one processor, to cause the at least one processor to perform the dialysis process based on the treatment recommendation.

20. The dialysis system of claim 18, the upper body oxygen consumption comprising a sum of oxygen consumption of upper body tissues, the upper body tissues comprising a brain, a heart, skeletal muscle, skin, or any combination thereof.

* * * * *